United States Patent [19]
Zavilla et al.

[11] Patent Number: 5,693,855
[45] Date of Patent: Dec. 2, 1997

[54] PROCESS FOR THE SYNTHESIS OF FLUORINATED SULFONIC ACIDS

[75] Inventors: John Zavilla, Vedbaek; Sven Ivar Hommeltoft, Hillerød, both of Denmark

[73] Assignee: Haldor Topsøe A/S, Lyngby, Denmark

[21] Appl. No.: 596,487

[22] Filed: Feb. 5, 1996

[30] Foreign Application Priority Data

Feb. 14, 1995 [DK] Denmark .................. 0167/95

[51] Int. Cl.$^6$ .................................. C07C 309/04
[52] U.S. Cl. .................................. 562/119
[58] Field of Search .......................... 562/119

[56] References Cited

U.S. PATENT DOCUMENTS

| | | | |
|---|---|---|---|
| 2,732,398 | 1/1956 | Brice et al. | 260/503 |
| 2,877,267 | 3/1959 | Van Dyke Tiers et al. | 260/543 |
| 3,542,864 | 11/1970 | Koshar | 260/543 |
| 3,919,295 | 11/1975 | Wechsberg et al. | 260/501 |

FOREIGN PATENT DOCUMENTS

| | | |
|---|---|---|
| 1573537 | 7/1969 | France . |
| 1668584 | 2/1968 | Germany . |
| 1912738 | 3/1969 | Germany . |
| 2725211 | 6/1977 | Germany . |
| 4208364 | 3/1992 | Germany . |
| 4218562 | 6/1992 | Germany . |
| 4226758 | 8/1992 | Germany . |

OTHER PUBLICATIONS

Qiu, et al. J. Fluorine Chem., 62(2–3), 273–81 1993.

*Primary Examiner*—Joseph Conrad
*Attorney, Agent, or Firm*—Ostrolenk, Faber, Gerb & Soffen, LLP

[57] ABSTRACT

Process for the preparation of a fluorinated sulphonic acid compound by hydrolysis of a corresponding fluorinated sulphonyl fluoride in the presence of a tertiary amine, comprising steps of (a) recovering a mixture of a salt of the fluorinated sulphonic acid with the tertiary amine and an ammonium fluoride salt of the tertiary amine;
(b) distilling off the tertiary ammonium fluoride salt and leaving a distillation remanence containing the salt of the fluorinated sulphonic acid with the tertiary amine; and
(c) recovering the fluorinated sulphonic acid compound from the distillation remanence.

4 Claims, No Drawings

PROCESS FOR THE SYNTHESIS OF FLUORINATED SULFONIC ACIDS

The present invention is directed to the preparation of fluorinated sulfonic acid compounds. In particular, the invention concerns certain improvements in the recovery of fluorinated sulfonic acid salts obtained during hydrolysis of fluorinated sulfonyl fluorides being an important step in the preparation of fluorinated sulphonic acids.

The usual synthesis route of fluorinated sulfonic acids involves hydrolysis of fluorinated sulphonyl fluorides, whereby a mixture of salts comprising a fluoride salt and a salt of the fluorinated sulfonic acid is obtained.

Fluorinated sulfonyl fluorides may be prepared in several ways, like electrochemical fluorination of corresponding alkane sulfonyl halides or cyclic sulfones in anhydrous HF (U.S. Pat. No. 2,732,398, DE Offenlegungsschrift No. 2,725,211, DE Offenlegungsschrift No. 1,912,738, DE Offenlegungsschrift No. 4,208,364, DE Offenlegungsschrift No. 4,218,562 and DE Offenlegungsschrift No. 4,226,758). Furthermore, it is known to prepare perfluorinated sulfonyl fluorides by addition of sulfuryl difluoride or sulfuryl chloride fluoride to fluoro-olefins (Great Britan Patent No. 1,189,562, U.S. Pat. No. 2,877,267, DE Auslegenschrift No. 1,668,584, FR Patent No. 1,573,537, U.S. Pat. No. 3,542, 864).

Hydrolysis of sulfonyl fluorides is in the known preparation processes performed by contacting the fluorides with an aqueous alkaline solution, such as solutions of KOH, NaOH or $NH_4OH$. The product from the hydrolysis step is an aqueous solution of salts, from which a salt of the fluorinated sulfonic acid is recovered as a solid.

Further synthesis steps involve distillation of the anhydrous salt of the fluorinated sulfonic acid by use of a strong acid such as concentrated sulfuric acid to anhydrous fluorinated sulfonic acid. Prior to distillation, HF being formed during the distillation has to be removed because of its corrosive nature. Removal of HF is usually accomplished by precipitation of fluoride salts of HF with low solubility, such as a barium salt, or extraction of fluorinated sulfonic acid salt from a mixture of salts from the hydrolysis step. In both cases, the known preparation processes involve handling of solids and drying of salts, which complicates the processes.

It has now been found that preparation of fluorinated sulfonic acids is much improved, when carrying out hydrolysis of corresponding sulfonic fluorides in presence of a tertiary amine and distilling off formed tertiary ammonium fluoride salts being formed during hydrolysis. The fluorinated sulfonic acid compound may then be recovered from the residue of the distillation step.

In accordance with the above finding, this invention provides a process for the preparation of a fluorinated sulfonic acid compound by hydrolysis of a corresponding fluorinated sulfonyl fluoride in presence of a tertiary amine, comprising further steps of
(a) recovering a mixture of a salt of the fluorinated sulfonic acid with the tertiary amine and an ammonium fluoride salt of the tertiary amine;
(b) distilling off the ammonium fluoride salt and leaving a distillation residue containing fluorinated sulfonic acid salt with the tertiary amine; and
(c) recovering the fluorinated sulfonic acid compound from the distillation residue.

The sulfonic acid compound may finally be recovered by protonization of the residue with a proton donating acid and distilling off the fluorinated sulfonyl acid compound from the protonized residue.

Alternatively, the residue is alkalized with an alkaline solution and the tertiary amine separated from the residue prior to the protonization.

During the distillation, the tertiary ammonium fluoride salt is distilled off in the form of a poly-HF salt with the formula $[\text{t-amine H}]^+[F(HF)n]^-$, where n is typically about 2.

Certain poly-HF salts are more volatile than their starting tertiary amines. As an example triisooctylamine having a boiling point of 150°–160° C. at 0.2 mm Hg is less volatile than its poly-HF salt with a boiling point of about 100° C. at the same pressure, whereas the poly-HF salt of tributylamine is less volatile (BP 100°–105° C. at 3 mm Hg) than tributylamine (BP 60°–65° C. at 3 mm Hg).

When employing tertiary amines, which form during distillation poly-HF salts with a lower boiling point, a substantially quantitative removal of fluoride salts is provided by the above process. Preferred tertiary amines are those having a boiling point over 200° C., most preferably over 250° C. at atmospheric pressure.

EXAMPLE 1

42.2 g of a 1:1 mixture of tributylammonium perfluorobutane-1-sulfonate ($CF_3CF_2CF_2CF_2SO_3HNBu_3$) and tributylammonium hydrofluoride ($FHNBu_3$) (prepared by reaction of perfluorobutane 1-sulfonyl fluoride with less than 1 equivalent of water in the presence of an excess of tributyl amine) were distilled at 0.06 psi (3 mm Hg). At a distillation temperature of 61°–63° C. 6.9 g of a colorless liquid (tributyl amine) were collected and at 102° C. by 5.1 g tributyl amine poly-HF salt. After the distillation, 26.3 g of a brown salt (tributylammonium perfluorobutane-1-sulfonate) remained, which crystallized upon cooling. Fluoride content of the sulfonic acid salt: 0.12%.

EXAMPLE 2

36.7 g of a 1:1 mixture of trietylammonium perfluorobutane-1-sulfonate ($CF_3CF_2CF_2CF_2SO_3HNEt_3$) and triethylammonium hydrofluoride ($FHNEt_3$) (prepared by reaction of perfluorobutane 1-sulfonyl fluoride with less than 1 equivalent of water in the presence of excess of triethyl amine) were distilled at 0.08 psi (4 mm Hg). 8.5 ml triethylamine were trapped in a freezing trap (F content: 530 ppm). At 94°–97° C. 3.7 g of a clear yellow liquid were collected, which was identified as triethylamine poly-HF salt. After the distillation, 30.4 g of a dark liquid salt (triethylammonium perfluorobutane-1-sulphonate) remained. Fluoride content of the sulfonic acid salt: 0.056%.

EXAMPLE 3

43.1 g of a 1:1 mixture of triisooctylammonium perfluorobutane-1-sulfonate ($CF_3CF_2CF_2CF_2SO_3HN(i-Oct)_3$) and triisooctylammonium hydrofluoride ($FHN(i-Oct)_3$) (prepared by reaction of perfluorobutane 1-sulfonyl fluoride with less than 1 equivalent of water in the presence of an excess of triisooctyl amine) were distilled at 0.15 mmbar leaving 20.2 g triisooctylammonium perfluorobutane-1sulfonate with a fluoride content of 360 ppm. Additional triisooctylamine was added and distilled off at 0.15 mbar leaving 17.9 g triisooctylammonium perfluorobutane-1sulfonate as a yellow highly viscous liquid with a fluoride content of 30 ppm.

We claim:

1. Process for the preparation of a fluorinated sulfonic acid compound by hydrolysis of a corresponding fluorinated sulfonyl fluoride in the presence of a tertiary amine, comprising the steps of:

(a) dissolving a fluorinated sulfonyl fluoride in the tertiary amine;

(b) recovering a mixture of a salt of the fluorinated sulfonic acid with a tertiary amine and a liquid ammonium fluoride salt of the tertiary amine;

(c) distilling off the tertiary ammonium fluoride salt and leaving a distillation residue containing the liquid salt of the fluorinated sulfonic acid with the tertiary amine; and (d) recovering the fluorinated sulfonic acid compound from the distillation residue.

2. The process of claim 1, wherein the tertiary amine has a boiling point of at least 200° C.

3. The process of claim 1, wherein the tertiary amine has a boiling point of at least 250° C.

4. The process of claim 1, wherein the tertiary amine is selected from the group of tertiary amines having a boiling point over 200° C., whereby, during distillation in step (b), poly-HF salts with a lower boiling point than the tertiary amine are formed.

* * * * *